United States Patent
Alinsod et al.

(10) Patent No.: US 11,219,762 B2
(45) Date of Patent: Jan. 11, 2022

(54) THERAPEUTIC DEVICE FOR FEMALE GENITAL PREDICTIVE PERMEATION

(71) Applicant: VITALITY CONCEPTS INTERNATIONAL LTD., Basel (CH)

(72) Inventors: Red M. Alinsod, Laguna Beach, CA (US); Heinz R. Gisel, Carlsbad, CA (US); Frank W. Vanesky, Vista, CA (US)

(73) Assignee: VITALITY CONCEPTS INTERNATIONAL LTD., Basel (CH)

( * ) Notice: Subject to any disclaimer, the term of this patent is extended or adjusted under 35 U.S.C. 154(b) by 234 days.

(21) Appl. No.: 16/291,501

(22) Filed: Mar. 4, 2019

(65) Prior Publication Data

US 2020/0282211 A1 Sep. 10, 2020

(51) Int. Cl.
*A61N 1/32* (2006.01)
*A61M 31/00* (2006.01)
*A61N 1/05* (2006.01)
*A61M 37/00* (2006.01)

(52) U.S. Cl.
CPC .............. *A61N 1/327* (2013.01); *A61M 31/00* (2013.01); *A61M 37/00* (2013.01); *A61N 1/0524* (2013.01); *A61M 2037/0007* (2013.01); *A61M 2202/0415* (2013.01); *A61M 2202/0427* (2013.01); *A61M 2210/1475* (2013.01)

(58) Field of Classification Search
CPC ............................... A61N 1/327; A61N 1/0524
USPC ........................................................... 604/20
See application file for complete search history.

(56) References Cited

U.S. PATENT DOCUMENTS

| | | | | |
|---|---|---|---|---|
| 5,875,778 A | * | 3/1999 | Vroegop | A61N 1/0524 607/138 |
| 7,010,343 B2 | | 3/2006 | Bemabei | |
| 7,083,580 B2 | | 8/2006 | Bemabei | |
| 7,471,979 B2 | | 12/2008 | Bemabei | |
| 2013/0110220 A1 | * | 5/2013 | Brown | A61N 1/326 607/149 |
| 2013/0184792 A1 | * | 7/2013 | Simon | A61N 1/0408 607/115 |
| 2016/0114154 A1 | * | 4/2016 | Bozzarelli | A61N 1/0524 607/41 |
| 2017/0056637 A1 | * | 3/2017 | Unger | A61N 1/303 |

* cited by examiner

*Primary Examiner* — Brandy S Lee
*Assistant Examiner* — Nidah M Hussain
(74) *Attorney, Agent, or Firm* — Neil K. Nydegger, Esq.

(57) ABSTRACT

A system and method are provided for performing predictive permeation on the skin of a patient, particularly where the skin has no corneum. For this purpose, a device is provided which has an elongated probe, with an electrode array that extends along an active segment of the probe. Also, a voltage source is connected to the electrode array to generate an electric field. Operationally, an electro-conductive emulsion is applied onto the skin of the patient where the predictive permeation procedure is to be performed and the probe is positioned to contact the skin to be treated. The emulsion then interacts with the electric field that is generated by the electrode array to increase the permeability of the skin. Particles from a blood sample of the patient are included in the emulsion, and are introduced into the skin during the predictive permeation procedure to increase skin density.

15 Claims, 2 Drawing Sheets

THERAPEUTIC DEVICE FOR FEMALE GENITAL PREDICTIVE PERMEATION

FIELD OF THE INVENTION

The present invention pertains generally to systems and methods that involve dermatological therapy. More particularly, the present invention pertains to predictive permeation of the skin to introduce a patient's own blood platelets into skin cell tissue. The present invention is particularly, but not exclusively, useful for employing predictive permeation techniques on skin having no corneum.

BACKGROUND OF THE INVENTION

Predictive permeation is a process in which an electric field is applied to a surface area of skin tissue for the purpose of increasing the skin's permeability. For dermatological applications, this increase in permeability results when temporary pores are created in the skin tissue by an applied electric field. In particular, the pores that are created allow substances (particles) to be introduced into the tissue that will increase the density of the skin for therapeutic and/or cosmetic purposes.

It is known that the efficacy of the electric field which is created for a predictive permeation procedure will be enhanced by applying an electro-conductive emulsion to the surface area of the skin that is to be treated. Preferably, particles in the emulsion used for the present invention will include a Platelet Rich Plasma (PRP) containing platelets taken from a sample of the patient's own blood. As mentioned above, when introduced into the skin of the patient, these particles will increase the skin's density. Other components for possible inclusion in the emulsion include: Benzocaine, Lidocaine Tetracaine (BLT) numbing cream/gel/solution; Platelet Rich Plasma (PRP) and Amniotic Fluid; Hyaluronic Acid (HA); Collagen; Vitamin C; Retin A; Tranexamic Acid; Serum with Growth Factors; stem cells; and/or Steroids (estradiol/testosterone/progesterone, corticosteroids).

An important consideration for an operation of the present invention is the nature of the skin surface that is to be treated by predictive permeation. In particular, the skin surface area of interest for the present invention is skin which has no stratum corneum (i.e. the rough, horny, outer surface layer of the skin's epidermis). More specifically, the target tissue of interest for the present invention is the vaginal tissue of a female. Another, important consideration for the present invention is the electric field that is to be created for performing a predictive permeation procedure. Specifically, the voltage used to generate the electric field should be minimal in order to eliminate adverse heating effects on the skin of the patient. On the other hand, the vibrational effects that result can be beneficial for enhancing absorption of the emulsion and providing a calming influence for the patient.

The medical conditions that may benefit from using the present invention include both gynecological and dermatological conditions. For instance, GYN: 1) pain control; 2) Atrophy/GSM/spareunia/pelvic pain; 3) Vulvar Dystrophy (Lichen, Hyperplastic Dystrophy), 4) Reduced sensitivity, Orgasmic Dysfunction, 5) Vulvar darkening, and 6) potentially overactive bladder. Additionally, DERM: 1) Dermatitis/Eczema; 2) Atrophy; 3) Skin Laxity.

With the above in mind, it is an object of the present invention to provide a system and method for performing a predictive permeation procedure on a target area of a patient's skin tissue that effectively increases the density of skin in the target area. Another object of the present invention to provide a system and method for performing a predictive permeation procedure on a target area of a patient's skin tissue that minimizes or eliminates adverse heating effects and provides a calming influence on the patient during the predictive permeation procedure. Still another object of the present invention to provide a system and method for performing a predictive permeation procedure on a target area of a patient's skin tissue that is performed with an emulsion containing a Platelet Rich Plasma (PRP) taken from a sample of the patient's own blood. It is also an object of the present invention to provide a system and method for performing a predictive permeation procedure on a target area of a patient's skin tissue that uses a device which is simple to manufacture, is easy to use, and is comparatively cost effective.

SUMMARY OF THE INVENTION

A device for performing a predictive permeation procedure on the skin of a patient includes, in combination, an elongated probe, an electrode array mounted on the probe, and a voltage source connected with the electrode array for generating a pulsed electric field. The device also includes a handle that is affixed to a proximal end of the probe for manipulating the probe. A switch that can be manipulated by a user of the device is provided to selectively connect the voltage source to the electrode array.

Additionally, an electro-conductive emulsion is provided which can be applied to targeted tissue on the surface area of skin that is to be treated. Specifically, the emulsion is used for the purpose of enhancing an interaction between the pulsed electric field and target tissue in the skin surface area that is to be treated during a predictive permeation procedure. Preferably, the electro-conductive emulsion includes a Platelet Rich Plasma (PRP). In particular, the Platelet Rich Plasma (PRP) will include platelets from a blood sample of the patient's own blood. As envisioned for the present invention, it is these blood platelets that are introduced by predictive permeation to increase the density of the target tissue (e.g. vaginal tissue).

In detail, the elongated probe is preferably cylindrically shaped, and it has a proximal end and a distal end with a central axis extending between the two ends. An active segment is established on the probe's outer surface between the ends of the probe, and the electrode array is mounted on the probe in the active segment. For purposes of the present invention, the probe is dimensioned and formed for easy insertion into the vagina of a female patient to position the electrode array in direct contact with vaginal tissue.

With regard to the electrode array, it will preferably include two pairs of electrodes. A first pair of negative electrodes are positioned on the probe axially opposite to each other. A second pair of positive electrodes are also positioned on the probe opposite to each other. Further, electrodes of one pair are positioned equidistant from adjacent electrodes of the other electrode pair. Additional electrode pairs, however, are possibly incorporated as long as adjacent electrodes have opposite polarities. For example, with three electrode pairs, each "+" electrode would be flanked by two "−" electrodes. With regard to the pulsed electric field that is generated by the present invention during a predictive permeation procedure, the magnitude of the electric field is minimized in order to avoid adverse heating of the target tissue. With this in mind, the peak to peak voltage magnitude of the electric pulses generating the electric field is preferably in a range of 2-30 volts and a current range of 0.5 to 5 mA, with a pulse frequency range of 10 Hz to 15 kHz.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
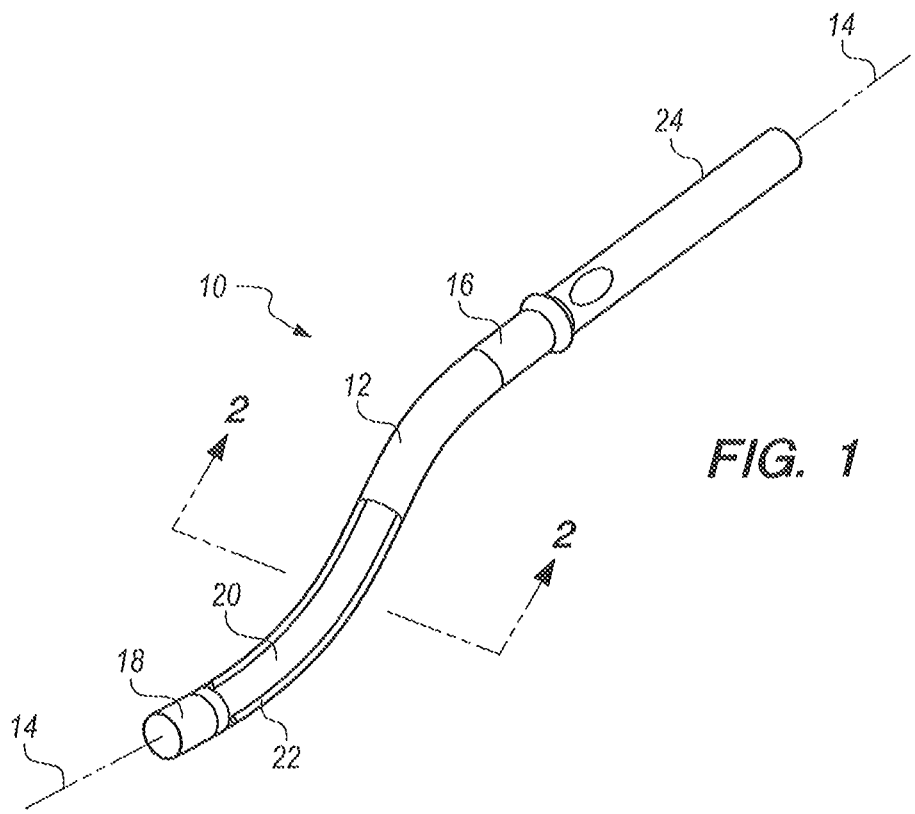
FIG. 1 is a side elevation view of a device in accordance with the present invention.

Referring initially to FIG. 1, a device for performing a predictive permeation procedure on skin tissue of a patient is shown in FIG. 1 and is generally designated 10. As shown, the device 10 includes an elongated probe 12 which defines a central axis 14 and has a proximal end 16 and a distal end 18. An active segment 20 is established on the probe 12, and an electrode array 22 is positioned on the probe 12 in the active segment 20. In this combination, the electrode array 22 is generally aligned with the axis 14.

Still referring to FIG. 1, the device 10 is shown to have a handle 24 that is affixed to the proximal end 16 of the elongated probe 12. Also, a switch (not shown) may be conveniently located to facilitate the activation of a voltage source 28 shown in FIG. 2. As envisioned for the present invention, the voltage source 28 may be incorporated into the handle 24 of the device 10, or located externally. In either case, it is to be appreciated that the switch will be operated to selectively connect the voltage source 28 with the electrode array 22.

Figure 2:
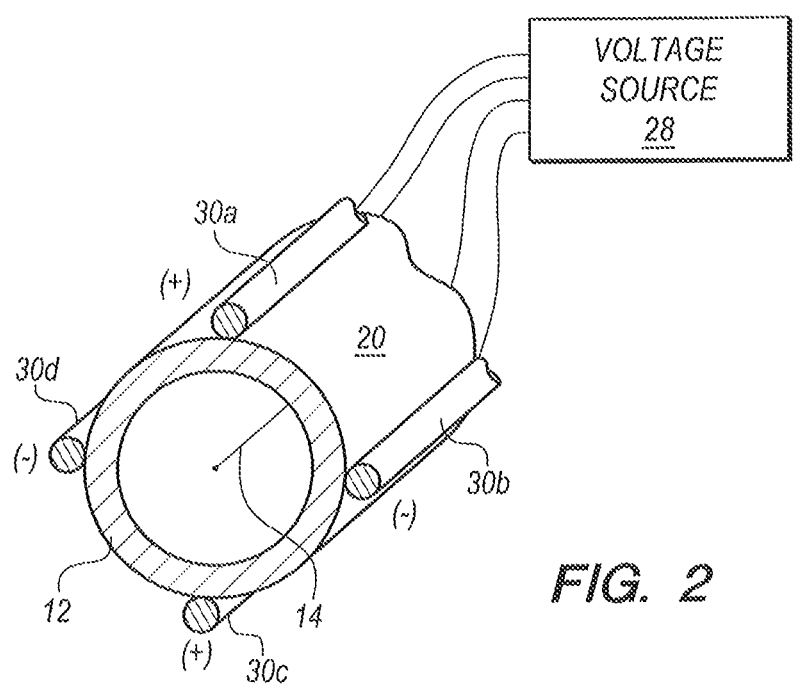
FIG. 2 is a partial perspective view of the device for the present invention as seen from a cross section plane of the device identified by the line 2-2 shown in FIG. 1, wherein portions are broken away for clarity.

Referring now to FIG. 2 it will be seen, in detail, that the electrode array 22 will preferably include four electrodes 30a-d that are generally aligned with the central axis 14 of the elongated probe 12, and they are positioned in its active segment 20. As indicated, in the configuration shown, the electrodes 30a and 30c will have a same polarity and the electrodes 30b and 30d will have a same polarity that is opposite to the polarity of the electrodes 30a and 30c. Further, all of the electrodes 30a-d will be connected to the voltage source 28 via the switch.

Figure 3:
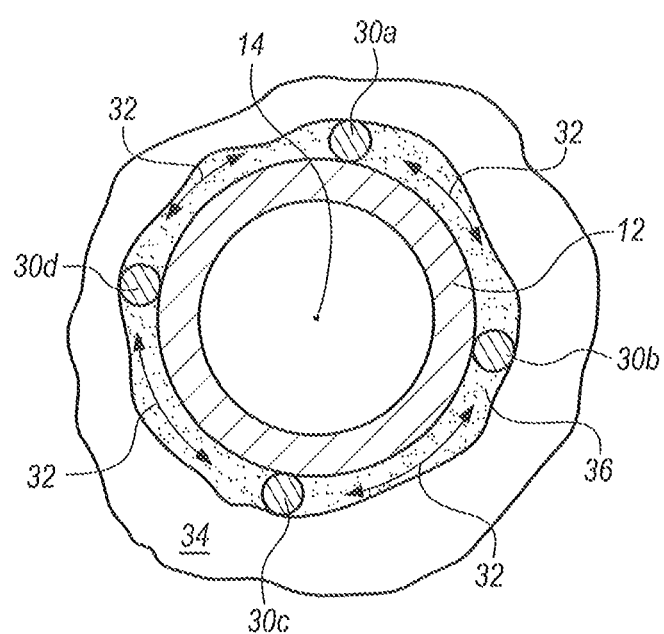
FIG. 3 is a cross section view of the device as also seen along the line 2-2 in FIG. 1 with the device operationally positioned in contact with a target tissue of a patient to perform a predictive permeation procedure on the target tissue.

With specific regard to the operational interaction between the voltage source 28 and the electrode array 22 (i.e. electrodes 30a-d), this combination will generate a pulsed electric field, E, which is represented by the arrows 32 in FIG. 3. Further, for purposes of the present invention, the electric field E will have predetermined electrical characteristics. In particular, the peak to peak voltage magnitude of the electric pulses that generate the pulsed electric field E is preferably in a range of 3-20 volts. Also, the electric field E will preferably have a pulse frequency range of 10 Hz to 15 kHz and a current in a current range of 0.5 to 5 mA.

In accordance with the present invention, a predictive permeation procedure will be best appreciated with reference to FIG. 3. Preferably, the target tissue 34 of interest for the present invention is a stratum corneum, such as the vaginal tissue of a female patient (not shown). In the event, it is envisioned that prior to performing a predictive permeation procedure, an electro-conductive emulsion 36 will be applied to the surface of the target tissue 34. Thus, when a device 10 is positioned against the target tissue 34, the electro-conductive emulsion 36 will surround the active segment 20 of the probe 12 with the emulsion 36 extending between adjacent electrodes 30. Consequently, when the voltage source 28 is activated by a manipulation of the switch to perform a predictive permeation procedure, the electric field E will be created in the emulsion 36 for its interaction with the target tissue 34.

An important consideration for the present invention is that the emulsion 36 will preferably include a Platelet Rich Plasma (PRP). Specifically, the PRP will include platelets from a blood sample of the patient's own blood. These blood platelets can then be introduced by predictive permeation to increase the density of the target tissue 34.

While the particular Therapeutic Device for Female Genital Predictive Permeation as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A device for performing predictive permeation on the skin of a patient, wherein the skin is vaginal tissue having no corneum, which comprises:

a voltage source for generating a pulsed electric field having a predetermined voltage magnitude;

an elongated probe defining a central axis, and having a proximal end and a distal end with an active segment established therebetween;

an electrode array oriented axially on the probe to extend along the active segment of the probe, wherein the electrode array includes a plurality of electrode pairs with electrodes of each electrode pair having a same polarity and each electrode is positioned on the probe between electrodes having a different polarity and wherein the voltage source is interconnected with the electrode array to selectively establish the pulsed electric field to symmetrically induce predictive permeation; and an electro-conductive emulsion including blood platelets applied onto the skin of the patient to interact with the electrode array and increase the permeability of the skin, for introducing the blood platelets into the skin during a predictive permeation procedure to increase skin density.

2. The device of claim 1 wherein the electrode array comprises:

a first pair of electrodes positioned on the probe axially opposite each other; and a second pair of electrodes positioned on the probe axially opposite each other, wherein each electrode of the second pair is positioned equidistant from electrodes of the first pair.

3. The device of claim 1 further comprising:

a handle affixed to the proximal end of the elongated probe for manipulating the probe.

4. The device of claim 3 wherein the blood platelets are taken from a blood sample of the patient to create the emulsion including a Platelet Rich Plasma (PRP).

5. The device of claim 1 wherein the peak to peak voltage magnitude of electric pulses generating the electric field is preferably in a range of 2-30 volts and a current range of 0.5 to 5 mA.

6. The device of claim 5 wherein the electric pulses generating the electric field have a pulse frequency range of 10 Hz to 15 kHz.

7. A device for performing predictive permeation on the skin of a patient, wherein the skin is vaginal tissue having no corneum, which comprises:
- a voltage source having a predetermined voltage magnitude;
- an elongated probe defining a central axis, and having a proximal end and a distal end with an active segment established therebetween;
- a first pair of electrodes having a first polarity positioned on the probe axially opposite each other;
- a second pair of electrodes having a second polarity positioned on the probe axially opposite each other, wherein each electrode of the second pair is positioned equidistant from electrodes of the first pair wherein the voltage source is interconnected with the first pair and with the second pair of electrodes to establish a pulsed electric field to symmetrically induce predictive permeation of the skin; and
- an electro-conductive emulsion including blood platelets applied onto the skin of the patient to interact with the electric field and increase the permeability of the skin, for introducing the blood platelets during a predictive permeation procedure to increase skin density.

8. The device of claim 7 wherein the electro-conductive emulsion includes particles to be introduced into the skin during the predictive permeation procedure to increase skin density.

9. The device of claim 8 wherein the particles are platelets taken from a blood sample of the patient to create an emulsion including a Platelet Rich Plasma (PRP).

10. The device of claim 9 wherein the peak to peak voltage magnitude of electric pulses generating the electric field is preferably in a range of 2-30 volts and a current range of 0.5 to 5 mA, with a pulse frequency in a range of 10 Hz to 15 kHz.

11. A method for performing predictive permeation on the skin of a patient, wherein the skin is vaginal tissue having no corneum, which comprises the steps of:
- applying a pulsed electro-conductive emulsion including blood platelets onto the skin to be treated;
- positioning an elongated probe in contact with the skin to be treated, wherein the elongated probe defines a central axis and has a proximal end and a distal end with an active segment established therebetween, and wherein an electrode array is oriented axially on the probe to extend along the active segment of the probe, wherein the electrode array includes a plurality of electrode pairs with electrodes of each electrode pair having a same polarity and each electrode is positioned on the probe between electrodes having a different polarity; and
- establishing a pulsed electric field with the electrode array to perform a symmetrically predictive permeation procedure wherein the permeability of the skin is increased to receive blood platelets from the emulsion into the skin to increase skin density.

12. The method of claim 11 further comprising the step of generating the electric field with a voltage source connected to the electrode array.

13. The method of claim 12 wherein the peak to peak voltage magnitude of electric pulses generating the electric field is preferably in a range of 2-30 volts and a current range of 0.5 to 5 mA, with a pulse frequency in a range of 10 Hz to 15 kHz.

14. The method of claim 12 wherein the blood platelets are in a blood sample from the patient, and the emulsion is a Platelet Rich Plasma (PRP).

15. The method of claim 12 wherein the electrode array comprises:
- a first pair of electrodes positioned on the probe axially opposite each other; and
- a second pair of electrodes positioned on the probe axially opposite each other, wherein each electrode of the second pair is positioned equidistant from electrodes of the first pair.

\* \* \* \* \*